United States Patent [19]

Palinczar

[11] Patent Number: 4,699,779
[45] Date of Patent: Oct. 13, 1987

[54] WATERPROOF SUNSCREEN COMPOSITIONS

[76] Inventor: Victor Palinczar, 435 Adeline St., Trenton, N.J. 08611

[21] Appl. No.: 829,949

[22] Filed: Feb. 18, 1986

[51] Int. Cl.$^4$ ............... A61K 7/42; A61K 7/44
[52] U.S. Cl. ................................. 424/59; 424/60; 514/937
[58] Field of Search ................................. 424/59, 60

[56] References Cited

U.S. PATENT DOCUMENTS

| | | | |
|---|---|---|---|
| 3,146,170 | 8/1964 | Battista | 424/59 |
| 3,375,271 | 3/1968 | Catino et al. | 424/59 X |
| 3,670,074 | 6/1972 | Doner | 424/47 |
| 3,816,611 | 6/1974 | Eberhardt et al. | 424/47 |
| 4,349,532 | 9/1982 | Vanlerberghe et al. | 424/47 |

*Primary Examiner*—Dale R. Ore

*Attorney, Agent, or Firm*—Sachs & Sachs

[57] ABSTRACT

An effective aesthetic water-proof sunscreen composition which includes ultraviolet light protection to the skin includes water in an amount from 15% up to about 95% by weight, from about 1% to about 30% by weight of an active sunscreen agent, from about 0.1% to about 6.0% by weight of ethylcellulose, from about 0.01% to about 12% of weight by a surface active agent, and from about 0.03% to about 5.0% by weight of an alkaline dispersion promoting agent.

The composition may optionally contain up to about 25% by weight of water-soluble organic liquids; up to about 20% by weight of water-insoluble emollients; up to about 20% by weight of suspended particulate matter; up to 8% by weight of plasticizers; up to 5% by weight of a thickening agent; and up to about 3% by weight of fragrance oil.

35 Claims, No Drawings

4,699,779

WATERPROOF SUNSCREEN COMPOSITIONS

BACKGROUND OF THE INVENTION

1. Field of the Invention

This invention relates to novel sunscreen compositions which, when applied to the human skin provide protection against the harmful effects caused by ultraviolet radiation. More particularly, this invention relates to sunscreen compositions in the form of aqueous lotions and creams wherein an ultraviolet light-absorbing ingredient is placed on the skin and is provided with increased water resistant characteristics with the aid of a polymeric binder. Most particularly, this invention relates to sunscreen compositions that are water-proof and fulfill the guidelines established by the Food and Drug Administration, as listed in the Federal Register: Volume 43, Number 166.

2. Discussion of the Relevant Art

Sunscreen compositions are commonly used during outdoor activity. Many people have occupations which require them to be exposed to the sun for long periods of time. Others choose to use their free time in outdoor recreations e.g. sunbathing, playing golf, surfing, fishing, skiing and swimming. All of these activities promote perspiration or allow the body to come in contact with water. Numerous sunscreen compositions have been developed which absorb ultraviolet light in a region of 280 to 320 nanometers (2800–3200 Angstroms; referred to as the "erythemal region") to protect the human body against this radiation that produces erythema and skin cancer, whether the source be from the sun or from man made devices. These compositions also incorporate ultraviolet absorbing agents that absorb in the region between 320 and 380 nanometers (3200–3800) Angstroms) and should be resistant to removal from the skin by perspiration or water in order to broaden and prolong their effectiveness.

Numerous substantive sunscreen agents, and substantive and water-resistant sunscreen compositions are available today. Development of substantive sunscreen agents and sunscreen compositions containing these substantive agents are illustrated in U.S. Pat. No. 3,864,473 issued to Cicendelli; U.S. Pat. No. 4,004,074 issued to Gerecht; and U.S. Pat. No. 4,256,664 issued to Epstein. These compositions make use of sunscreen agents that are not approved by the FDA and their topical use is limited.

No known sunscreen agent, that achieves a degree of water-resistancy, has been approved by the Food and Drug Administration. FDA approved sunscreen agents have, however, been incorporated into compositions which upon application to the skin physically keep the sunscreen agent on the skin during perspiration or immersion in water. The majority of these compositions make use of polymeric materials that are either emulsified in the composition or carried to the skin by a vehicle in which a continuous polymeric film is cast on the skin.

The use of an acid form of a cross-linked co-polymer of ethylene-maleic anhydride composition in the form of a gel is illustrated in U.S. Pat. No. 3,821,363 issued to Black. Compositions and methods are described in U.S. Pat. No. 3,895,104 issued to Karg in which polyamide resinous material is used as a film former. The use of acrylate/acrylic acid co-polymer compositions in the form of oils and emulsions are illustrated in U.S. Pat. No. 4,172,122 issued to Kubik. In U.S. Pat. No. 4,254,102 issued to Kaplan there is described the use of compositions containing hydroxyethyl-cellulose in conjunction with a surface active agent and a fatty alcohol. In U.S. Pat. No. 4,193,989 issued to Teng, there is described gel compositions of hydroxypropyl cellulose acetate as the film former.

Known compositions that make use of polymers to form a continuous polymeric film in which the active sunscreen agent is homogeneously dispersed throughout the matrix of the film have numerous disadvantages. Aqueous based compositions in which the polymer is usually emulsified have long drying rates on the skin, foam on the skin during application and during the drying cycle leave the skin feeling tacky. These compositions, if not fully dried, also have a tendency to allow particulate matter, such as beach sand, to adhere to the skin. Furthermore, the water-resistant properties of these aqueous based compositions are decreased if they are not fully dried before perspiration or entry into water. The formation of a continuous protective film n the skin is prevented by compositions which make use of solvent systems because they cannot tolerate large amounts of oil and other emollients. Without the use of emollients in compositions containing alcohols, the skin may become dry and irritated. Generally these compositions are also formulated in thin solutions with low viscosities which make them difficult to apply to the skin in an even manner.

Compositions, which make use of an ethylcellulose polymer, in combination with ethanol as a solvent and are effective in resisting water wash off, are products currently marketed by Carter-Wallace, Inc., New York, N.Y., under the trade names of BLOCK OUT and SEA & SKI. These compositions, however, are low in viscosity, contain high levels of silicone fluids and are costly to produce. They are also difficult to apply to the skin evenly thus permitting spot burning to occur, which may result in extreme pain and blistering of the skin. This effect is more pronounced with individuals having fair complexions and who normally use sunscreen products having high SPF (Sun Protection Factor) values. Water-resistant compositions described heretofore that contain high levels of solvents that are currently being marketed in addition to being difficult to apply to the skin evenly, lack the ability to be made in a range of viscosities, thus limiting the formulator in his selection of ingredients to be used in a composition and separate systems must be developed to fulfill the needs of the consumer.

Furthermore, compositions having high solvent concentrations lack the ability to homogeneously suspend particulate matter throughout the matrix of the composition thereby preventing the use of insoluble solid ingredients which have a tendency to prevent ultraviolet radiation from being absorbed by the skin.

The present invention overcomes the shortcomings of known water-resistant sunscreen compositions by incorporating ingredients that resist removal of the active sunscreen agent and particulate suspended matter, that reflect and/or absorbs ultraviolet radiation, by perspiration and water when applied to the skin. The present invention, in combination with ingredients that, allow the composition to be solvent free in nature with a range of viscosities, have the ability to suspend insoluble particulate matter, that can be applied to the skin evenly and easily, that protect the skin from the harmful effects of the sun's radiation, and that dry quickly without leaving the skin feeling tacky. There is a need for such a product for both health and cosmetic reasons. Ingredients may be available which exhibit one or more of these desired attributes but the combination of these attributes, for use in preparing water-proof sunscreen systems has not been demonstrated. Ingredients fulfilling these requirements, which have not been used previous to this invention in water-proof solvent free sunscreen compositions are the combination of active sunscreen agents, ethylcellulose polymers, alkaline dispersion promoting agents, surface active agents and water.

SUMMARY OF INVENTION

This invention relates to very effective, highly aesthetic water-proof sunscreen composition in the form of aqueous lotions and creams which provide ultraviolet light protection to the skin comprising water in an amount of up to 95% by weight, from about 1% to about 30% by weight of an ultraviolet radiation absorber, i.e., an active sunscreen agent, from about 0.1% to about 6.0% by weight of ethylcellulose polymer, from about 0.03% to 5.0% by weight of an alkaline dispersion promoting agent, and from about 0.01% to 12% by weight of a surface active agent.

The compositions may optionally contain from about 0% to about 8% by weight of a plasticizer, from about 0% to about 20% by weight of water-insoluble emollients, from about 0% to about 20% by weight of suspended particulate matter, from about 0% to about 25% by weight of water-soluble organic liquids, from 0% to about 5.0% by weight of thickening agents and from 0% to about 3% of fragrance oil.

DETAILED DESCRIPTION OF THE INVENTION

It has been discovered that highly effective, non-irritating cosmetically aesthetic water-proof compositions in the form of lotions and creams containing water, a polymeric film former such as ethylcellulose, active sunscreen agents, a surface active agent and an alkaline dispersion promoting agent are prepared by first preparing an ethylcellulose dispersion which is made by combining the ethylcellulose polymer with a suitable solvent, an active sunscreen agent and a fatty acid and/or a surface active agent and heating the materials in a vessel to approximately 75-80 degrees C. with continuous agitation until a homogeneous solution is obtained. The temperature of the mixture is then lowered to about 70-75 degrees C. at which time an ammoniacal-water solution, which has been previously heated to about 70 degrees C., is added with continuous agitation. The aqueous phase must be maintained at nearly 70 degrees C., and the addition must be made slowly, in a drop-wise manner. The aqueous phase should be added no faster than it can be absorbed into the ethylcellulose phase. Too rapid addition of the ammoniacal-water solution phase will result in the formation of an ethylcellulose dispersion having large particles. This effect will cause the dispersion to be unstable and prevents the coalescing of the ethylcellulose polymer particles thereby negating the formation of a continuous water resistant film. As the ammoniacal-water solution is added to the ethylcellulose solution, colloidal particles of ethylcellulose polymer, and a soap of the fatty acid and ammonium hydroxide begin to form. The in-situ formation of the soap serves as a surface active agent in the present invention. If one desires not to prepare a soap in-situ for whatever reasons, a soap or any other surface active agent can be added directly into the ethylcellulose/solvent/active sunscreen agent solution. Upon completing the addition of the ammoniacal-water solution, an opaque off-white dispersion results. The solvent is then removed by distillation. The resulting solvent-free dispersion is then adjusted to a pH of about 9 with ammonium hydroxide and any water loss that occurred during the distillation is replaced. The dispersion at this time may be milled to form sub-micron particles of ethylcellulose polymer containing the active sunscreen agent. The resulting dispersion has a consistancy of "cream", free of any distinct particles and may then be combined in a variety of cosmetic bases which are fully described and illustrated hereinafter.

In another procedure for preparing an ethylcellulose dispersion, the ethylcellulose polymer is combined with the active sunscreen agent, surface active agents and heated to about 100-120 degrees C. in a closed vessel with agitation until a complete solution is formed. Upon forming a complete solution, the mixture is cooled to about 100 degrees C. at which time an ammoniacal-water solution which has been previously heated to about 95 degrees C. in a separate closed vessel, is added to the ethylcellulose phase with extreme care and in a drop-wise manner. The rate of addition should be no faster than it can be absorbed into the ethylcellulose phase. Too rapid of an addition will result in the formation of a solid plastic-rubbery mass. Upon completing the addition of the aqueous phase, the mixture is cooled to room temperature with milling if desired, to produce colloidal particles having an average diameter of less than 2 microns. The dispersion is then adjusted with ammonium hydroxide to a pH of about 9 and it can be used as such or in combination with various cosmetic bases which will be fully illustrated hereinafter.

The techniques and formulations used in the preparation of aqueous resin dispersions are well known to the arts and are illustrated by H. W. Warson in "The Application of the Formation of Resin Emulsion." No known art, previous to this discovery, however, describes the in-situ formation of an ethylcellulose polymer dispersion in conjunction with active F.D.A. approved sunscreen agents to form water-proof sunscreen compositions.

Although the procedures described heretofore for preparing ethylcellulose dispersions containing an active sunscreen agent, for the purpose of producing a water-proof sunscreen composition, are considered highly functional and unique, they may be considered difficult and hazardous to manufacture to those who are not familiarized with such procedures. This is especially true for cosmetic manufacturers who produce sunscreen products. To manufacture and/or store such a dispersion for use in sunscreen products may also be too cumbersome and costly especially for manufacturers who are not equipped to prepare such a dispersion or whose needs are not adequate to produce large volumes of a stock dispersion.

To eliminate these concerns and as an optional means for obtaining an ethylcellulose dispersion, it has been discovered that several recently developed ethylcellulose dispersions are commercially available and are marketed by DOW Chemical, Midland, Mich. being sold under the experimental trade names of XD-30543.40 and XD-30543.30. Although these dispersions do not contain active sunscreen agents, they can be combined with numerous sunscreen agents, to form water-resistant sunscreen compositions in a similar manner as the ethylcellulose/active sunscreen dispersions described in the present invention.

It should be clearly understood that the use of a pre-made ethylcellulose dispersion manufactured by DOW does not depart from the scope and spirit of this present invention. The use of a pre-made ethylcellulose dispersion in combination with an active sunscreen agent can be used as such on the skin or can be incorporated into a variety of cosmetic bases which will be illustrated hereinafter.

It has further been discovered that the composition may additionally contain water-insoluble emollients which serve to prevent the skin from drying, leaving the skin feeling smooth and soft. The water-insoluble emollients also add body to the composition and decrease the tackiness of the composition during dryout. It has still further been discovered that the composition may contain suspended particulate matter which serve as an auxiliary means to reflect and/or filter ultraviolet radiation. The suspended particulate matter may also serve as a cosmetic additive to make the composition more glamorous in the container and/or on the skin. It has additionally been discovered that the composition may contain water-soluble organic liquids which serve to increase the solubility of water-insoluble ingredients used in the present invention. It has still additionally been discovered that the composition may contain thickening agents which serve to increase the viscosity of the composition allowing for the composition to be made in a variety of viscosities ranging from thin lotions to thick creams. The composition may also contain fragrance oil. These ingredients are more specifically described below.

While applicant does not wish to be limited by any theory of the mechanism of the activity of the invention, it is believed that the ethylcellulose dispersion, when properly made, consists of sub-micron particles of sunscreen agent/ethylcellulose polymer. The active sunscreen agent is absorbed or imbibed by the ethylcellulose. Upon evaporation of the volatile ingredients contained in the compositions, the sub-micron particles of ethylcellulose containing the active sunscreen agent, coalesce and form a continuous, impervious water-resistant film consisting of a high ratio of active sunscreen agents to organic and inert ingredients.

This discovery surpasses the use of other sunscreen compositions containing a polymeric film former that make use of solvents to dissolve polymer; this is especially true for sunscreen products containing ethylcellulose. Solvent use increases cost, irritation potential, flammability and the common toxicological problems associated with many solvents either during use of these products or in their manufacturing. The use of an aqueous microdispersion of ethylcellulose eliminates these concerns. The water-insoluble film also helps prevent the loss of the active sunscreen agents by physical abrasion and is uneffected by bodily salts expelled from the body during perspiration. It is believed that the ethylcellulose film allows perspiration to pass through the continuous film in the vapor state, thereby leaving the film intact and continuous. It is further believed that the film in addition to containing the active sunscreen agent at a high ratio of sunscreen agent to ethylcellulose polymer prevents the migration of the active sunscreen agent from the matrix of the film keeping the active sunscreen agent on the surface of the skin, thereby decreasing percutaneous absorption through the skin of the active sunscreen agent. It is therefore believed that the combination of these actions cause these compositions to be effective for long periods of time and to resist removal by water and perspiration.

THE POLYMERIC FILM-FORMER

Polymers, such as the ETHOCELS manufactured by (THE DOW CHEMICAL COMPANY, MIDLAND, MICH.) are derivatives of cellulose in which the anhydroglucose unit is substituted with ethoxyl group having a softening point at about 130 degrees C. to about 170 degrees C.; a melting point at about 160 degrees C. to about 220 degrees C. These polymers are further described by the degree of substitution of the anhydroglucose unit, which contains three reactive hydroxyl sites. Substitution of all hydroxyl groups with ethoxyl groups would have a degree of substitution of 3. If half of the anhydroglucose unit of the polymer were substituted with three exthoxyl groups and the other half were substituted with two ethoxyl groups, leaving one unsubstituted hydroxyl group on every other anhydroglucose unit, the ethylcellulose would have a degree of substitution of 2.5. The difference in physical properties of ethylcellulose results from variation in the degree of etherification. Ethylcellulose containing 2.25 to 2.58 ethoxyl groups per anhydroglucose units are further referred to by the ethoxyl content of 45% to 52%, respectively. The polymers of ethylcellulose are further described by different viscosities in which the length of the polymer's molecule increases. The preferred polymers of ethylcellulose are those polymers having an ethoxyl content between 48% to about 49.5% and are sold under the trade name (ETHOCEL "Standard" ethoxy) having viscosity designations between 4 and 50. The present invention may contain from about 0.1% to about 6% by weight of these ethylcellulose polymers or a mixture thereof. The preferred amount of ethylcellulose polymer is from about 0.5% to about 2% by weight of the total composition. The chemical composition of polymers, especially those derived from cellulose is highly complex and usually contain a broad spectrum of molecular weight species. For this reason applicant wishes not to be limited to the ethylcellulose polymers mentioned in the present invention.

THE ACTIVE SUNSCREEN AGENT

Any active sunscreen agent, capable of absorbing the harmful effects of ultraviolet radiation which is non-irritating, non-toxic and is compatible with the ingredients used in the composition and which when applied to the skin are homogeneously dispersed throughout the film formed, by the ethylcellulose polymer, can be used. Active sunscreen agents that meet these criteria are: PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4-[bis(hydroxypropyl)]-aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); Oxybenzone (2-hydroxy-4-methoxybenzophenone); Padimate A (amyl p-dimethylaminobenzoate); Padimate O (octyl p-dimethylaminobenzoate); 2-phenylbenzimidazole-5-sulfonic acid); Sulisobenzone (5-benzoyl-4-hydroxy-2-methoxybenzenesulfonic acid); triethanolamine salicylate; 4-tert. butyl-4-methoxy-dibenzoylmethane; and benzalphthalide.

The present invention may contain from about 1% to about 30% by weight of these active sunscreen agents or a mixture thereof. The preferred total amount of the active sunscreen agent is dependent upon the SPF value (sun protection factor) desired to be obtained. The preferred sunscreen agents in the present invention are Padimate O in amounts from 2% to about 10% by weight; Padimate A in amounts from 1% to about 8% by weight; 2-ethylhexyl salicylate in amounts from 3% to about 8% by weight; ethylhexyl p-methoxycinnamate in amounts from 2% to about 8% by weight; Dioxybenzone from 1% to about 5% by weight and Oxybenzone from 1% to about 7% by weight.

ALKALINE DISPERSION PROMOTING AGENT

Any alkaline, soluble in water, capable of promoting the formation of the ethylcellulose dispersion by allowing the formation of hydrogen bonding, which volatilizes from the composition during use, which when used in the needed amounts, is non-irritating, non-toxic and is compatible with ingredients used in the composition which when applied to the skin allows the formation of a continuous, water-resistant polymeric film in which the active sunscreen agent is homogeneously dispersed, can be used. Alkaline dispersion promoting agents that meet these criteria are low molecular weight $C_3$–$C_6$ amines such as diisopropanol-amine and ammonium hydroxide.

The preferred alkaline dispersion promoting agent is ammonium hydroxide. The present composition may contain from 0.03% to 5.0% by weight of the alkaline dispersion promoting agent. The preferred amount of alkaline dispersion promoting agent is 0.1% to about 1.0% by weight.

THE SURFACE ACTIVE AGENT

Surface active agents used in the present composition are defined as surface active agents that (1) allow for the formation of the ethylcellulose dispersion in combination with an active sunscreen agent, an alkaline dispersion promoting agent and water or (2) allow for the formation of emulsions preferably water-in-oil emulsion, which are viscous lotions or creams consisting of the ethylcellulose dispersion, active sunscreen agent, water and any optional ingredient used in the compositions of the present invention.

The function of the surface active agents used in the present invention which are used for the purpose of forming the ethylcellulose dispersion is to physically unite the ethylcellulose polymer, active sunscreen agent and water, which are not compatible under normal conditions, by decreasing the interfacial tension, and allowing the formation of hydrogen bonding in which sub-micron particles of ethylcellulose/active sunscreen agent are formed and remain suspended for long periods of time throughout the water media.

Any surface active agent, capable of allowing the formation of an ethylcellulose dispersion which is non-toxic, non-irritating and is compatible with ingredients used in the composition, which when applied to the skin allows for the formation of a continuous, water-resistant polymeric film in which the active sunscreen agent is homogeneously dispersed can be used. Examples of these surface active agents are selected from a group consisting of soaps of fatty acid such as ammonium myristate, triethanolamine stearate and potassium oleate; anionics such as sodium alkyl benzene sulfonates and sodium polyoxyethylene lauryl sulfates; and nonionics such as polyoxyethylene sorbitan monolaurates and polyoxyethylene nonyl phenyl ethers. The preferred primary surface active agents are ammonium myristate and potassium oleate. The preferred amounts of surface active agent used in the present composition for the purpose of forming the ethylcellulose dispersion is from 0.01% to about 2.0% and preferrably from 0.05% to about 1%.

Surface active agents which can be used in the present invention for the purpose of forming viscous lotion or cream emulsions are those which are non-irritating, non-toxic and are compatible with the ingredients used in the composition which when applied to the skin allow the formation of a continuous polymeric film in which the active sunscreen agent is homogeneously dispersed which are selected from a group consisting of anionic surfactants such as alkanolamides, and alkyl ether sulfates and nonionic surfactants such as ethers derived from the condensation of fatty acids and ethylene oxide. The preferred surface active agent are those which are nonionic in nature which have a tendency to form water-in-oil emulsions. To those skilled in the arts, there are numerous known varieties of nonionic surface active agents which will form such emulsions. Since the overall hydrophile-lipophile balance of an emulsion is the prime factor in emulsion formation, which includes all of the ingredients in the composition and most specifically those ingredients which are to be emulsified, applicant wishes not to be limited to any specific surface active agents. It will be further understood that the surface active agents provide excellent compatibility with an array of cosmetically acceptable ingredients, and any combination may be made without departing from the spirit and scope of this invention. The preferred amount of surface active agent used in the present composition for the purpose of forming an emulsion is from 2% to about 6% by weight.

THICKENING AGENTS

The present composition may also contain, as an optional ingredient, from about 0% to about 5% by weight of a thickening agent. Thickening agents, which can be used in the present invention are ingredients that have a propensity for water or similar hydroxyl donors, that allow the formation of strong hydrogen bonding, which results in expanding the molecule, forming a laminated network of thickening agent molecules producing an increase in the viscosity of the composition, which are non-irritating, non-toxic and are compatible with the ingredients used in the composition which when applied to the skin allow the formation of a continuous polymeric film in which the active sunscreen agent is homogeneously dispersed. Examples of such thickening agents are selected from a group consisting of synthetic polymers such as acrylic acid crosslinked polymer sold under the trade name of CARBOPOL by (B.F. GOODRICH; CLEVELAND, OHIO); hydroxyethylcellulose; hydroxypropylcellulose; poly(methyl vinyl ether/maleic anhydride) sold under the trade name by (GAF, INC., WAYNE, N.J.) as Thicken L; copolymer of methyl vinyl ether and maleic anhydride and sold under the trade name GAFTEX PT also by GAF; Natural gums such as Xanthan Gum; inorganic salts such as fumed silica, amorphous silica, sodium magnesium silicate and colloidal magnesium aluminum silicate. The preferred thickener is CARBOPOL, an acrylic acid crosslinked polymer. The preferred amount of the thickening agent is from 0.5% to about 2% by weight.

THE PLASTICIZER

The present composition may additionally contain as an optional ingredient from about 0% to about 8% by weight of a plasticizer and are usually in the liquid state at room temperature (about 22 degrees C.) and have a water solubility of less than 5.0% at 20 degrees C.

Plasticizers used in the present composition are usually referred to as substances that possess the property of preventing plastics (polymers) from becoming brittle and thereby losing a great degree of flexibility. This property becomes most important in the present invention in which the polymer forms a continuous impermeable film on the skin. Plasticizer use, in combination with polymers that form films, are needed to prevent cracking of the film after the solvent or carrier evaporates from the skin. More important, the plasticizers used in the present invention must be compatible with ethylcellulose and allow the polymeric film to be flexible enough to withstand constant body movement while allowing the film to adhere to the skin and resisting removal by water and perspiration. The plasticizer must further provide a good feel to the skin cosmetically; that is, it cannot be greasy or oily in nature. The plasticizer must also be non-toxic and non-irritating to the skin without having any inherent mal odor. Plasticizers used in the present invention are generally organic liquids. The chemical composition of plasticizers is complex and usually contain a broad spectrum of molecular weight species and reactive functional groups. For this reason applicant wishes not to be limited only to the plasticizers mentioned in the present invention. Preferred plasticizers are (but not limited to): esters such as dibutyl sebacate and dibutyl phthalate. The preferred amount of plasticizer in the present invention is from 0.2% to about 5% by weight.

WATER-SOLUBLE ORGANIC LIQUID

The present composition may additionally contain as an optional ingredient from about 0% to about 25% by weight of water soluble materials which are in the liquid state at room temperature (about 22 degrees C.) and have a water solubility of greater than about 2.25% at 25 degrees C. From these liquids a group of liquids have been selected which are organic in nature having a low degree of irritation and toxicity that are generally considered safe for topical use that (1) acts as co-solvents for the water-insoluble ingredients used in the composition; or (2) provide for faster drying rates or (3) act as humectants. Water-soluble liquids which can be used in the present invention which when applied to the skin allow the formation of a continuous polymeric film in which the active sunscreen agent is homogeneously dispersed are those selected from a group consisting of monohydric alcohols, such as ethanol and isopropanol; polyhydric alcohols such as propylene glycol and glycerin; ethers such as diethylene glycol monomethyl ethers, and diethylene glycol monoethyl ether, and homo-linear polymers of ethylene oxide. The preferred water-soluble organic liquid is ethanol. The preferred amount of water-soluble organic liquid is from 5% to about 15% by weight.

THE SUSPENDED PARTICULATE MATTER

The present composition may additionally contain, as an optional ingredient, from about 0% to about 20% by weight of suspended particulate solid matter which is insoluble in the ingredients used in the composition. From these solids a group of solids have been selected which are inert in the composition, having a low degree of irritation and toxicity, that are generally considered safe for topical use, that provide for a cosmetic benefit and reflect and/or absorb ultraviolet radiation. Solids that are used for cosmetic purposes are solid materials that produce a "glitter", "sparkle" or "pearlesant" effect when exposed to natural or artificial light. Preferred solids for cosmetic purposes include such solids as bismuth oxychloride, mica and colorized acrylic polyester. The preferred solid in the present composition, for cosmetic use, is the colorized acrylic polyester. The preferred amount of solid used for cosmetic purposes in the present invention is from 0.5% to about 10% by weight.

The preferred solid used in the present invention for the purpose of reflecting or absorbing ultraviolet radiation are solids such as zinc oxide, and titanium dioxide. These solids are generally used in a powder form in which the average particle size is less than 100 microns. The preferred amount of suspended particulate solid matter used in the present invention for the purpose of reflecting ultraviolet radiation is from about 5% to about 15% by weight.

THE WATER-INSOLUBLE EMOLLIENT

The present composition may additionally contain, as an optional ingredient, from about 0% to about 20% by weight of water-insoluble materials having a water solubility of less than about 1% at 25 degrees C. From these materials a group of compounds have been selected which are organic in nature having a low degree of irritation and toxicity, that are generally considered safe for topical use, that provide a softening or soothing effect on surface skin tissue are hereinafter referred to as the water-insoluble emollients in the present composition. Preferred water-insoluble emollients include fatty acids such as oleic and stearic; fatty alcohols such as cetyl, and hexadecyl (ENJAY); esters such as diisopropyl adipate, benzoic acid esters of $C_9$–$C_{15}$ alcohols, and isononyl iso-nonanoate; alkanes such as mineral oil; silicones; such as dimethyl polysiloxane and ethers such as polyoxypropylene butyl ethers and polyoxypropylene cetyl ethers. The most preferred water-insoluble emollients are: diisopropyl adipate, dimethylpolysiloxane 50 cst. and polyoxypropylene (14) butyl ether. The preferred amount of water-insoluble emollient is from about 2% to about 15% by weight, and most preferably from about 4% to about 10%.

The water-insoluble emollient can be used to control the rate of evaporation of the composition. In addition to providing emolliency, they also aid in controlling the amount of product deposited on the skin and the rigidity of the continuous polymer film. One skilled in the art will easily be able to adjust the cosmetic aesthetics and physical characteristics of the composition by combining various suitable water-insoluble emollients in the proper proportions with the ingredients of the composition mentioned hereintofore.

The water-proof sunscreen compositions of the present invention may be made in a variety of ways to those skilled in the art. One of the most suitable methods is to first prepare an ethylcellulose stock dispersion and then combining it with the desired remaining ingredients. One such procedure for preparing an ethylcellulose stock dispersion makes use of an ethylcellulose polymer (ETHOCEL STANDARD, vis 10 made by DOW CHEMICAL); a solvent (ethanol); an active sunscreen agent (Padimate O); a fatty acid (myristic acid—which is processed in-situ into a soap and functions as a surface active agent); and an alkaline dispersion promoting agent (ammonium hydroxide). In this procedure 5 parts of the ethylcellulose polymer, 20 parts of Paidmate O, and 2 parts of myristic acid and 25 parts of ethanol are placed in a 125 ml. erlenmeyer flask containing a magnetic stirring bar and affixed with a reflux condenser and a side arm adapter. The ingredients are heated to about 70–75 degrees C. with agitation until a complete solution is formed.

In a separate vessel 2 parts ammonium hydroxide (28% solution) and 21 parts of water are heated to about 70 degrees C and is transferred to a closed dropping flask having a ground joint compatible with the side arm adapter. The ammoniacal solution is then added to the ethylcellulose solution in a dropwise manner at a rate no faster than it can be absorbed into the ethylcellulose solution. Upon completion of the ammoniacal solution addition, the ethanol is distilled off from the mixture. To the resulting dispersion, ammonium hydroxide is added until a pH of about 9 is obtained. Any loss of water that occurred during the distillation, is then replaced, so that the total parts of the dispersion equals 50. To illustrate the ethylcellulose dispersion prepared using the foregoing procedure, the following examples are provided:

EXAMPLE 1

| INGREDIENTS | PERCENT BY WEIGHT |
| --- | --- |
| Ethylcellulose STD 10 vis | 10.0 |
| Padimate O | 40.0 |
| Ammonium Hydroxide - 28% solution | 4.0 |
| Myristic Acid | 4.0 |
| Water | 42.0 |
|  | 100.0 |

EXAMPLE 2

| INGREDIENTS | PERCENT BY WEIGHT |
| --- | --- |
| Ethylcellulose STD 10 vis | 10.0 |
| Padimate O | 20.0 |
| 2-Ethylhexyl Salicylate | 20.0 |
| Ammonium Hydroxide - 28% solution | 4.0 |
| Oleic Acid | 4.0 |
| Water | 42.0 |
|  | 100.0 |

In another procedure, where it is not desirable to prepare an ethylcellulose stock dispersion containing high levels of active sunscreen agent, an ethylcellulose polymer (ETHOCEL STD, vis 10), active sunscreen agents (Padimate O), a fatty acid (myristic) and an alkaline dispersion promoting agent (ammonium hydroxide) are combined without the use of a solvent. In this procedure 1 part of myristic acid is combined with 8 parts of Padimate O to 125 ml. erlenmeyer flask containing a magnetic stirring bar and heated to about 75 degrees C. with agitation, upon the formation of a complete solution, the ethylcellulose polymer is added and the mixture is heated to 100-120 degrees C. After the ethylcellulose polymer dissolves, the mixture's temperature is adjusted to about 100 degrees C. The flask is then fixed with a reflux condenser and a side arm adapter. In a separate vessel 1 part of ammonium hydroxide (28%) and 39 parts of water are heated to about 75 degrees C. and is added to the ethylcellulose/active sunscreen solution from a closed dropping flask which is placed on the side arm adapter. The ammoniacal solution is carefully added in a drop-wise manner at a rate no faster than it can be absorbed into the mixture. Upon completing the addition, the mixture is cooled to room temperature. Milling may be induced at this time if it is desired. At room temperature the pH of the dispersion is adjusted to about 9 with ammonium hydroxide. The dispersion can be used as such on the skin or combined with the optional ingredients. To illustrate the ethylcellulose dispersion prepared using the foregoing procedure, the following examples are provided:

EXAMPLE 3

| INGREDIENTS | PERCENT BY WEIGHT |
| --- | --- |
| Ethylcellulose STD vis 10 | 2.00 |
| Padimate O | 16.00 |
| Myristic Acid | 2.00 |
| Ammonium Hydroxide - 28% solution | 2.00 |
| Water | 78.00 |
|  | 100.00 |

EXAMPLE 4

| INGREDIENTS | PERCENT BY WEIGHT |
| --- | --- |
| Ethylcellulose STD vis 10 | 2.00 |
| Padimate O | 8.00 |
| Ethylhexyl p-methoxycinnamate | 8.00 |
| Myristic Acid | 2.00 |
| Ammonium Hydroxide - 28% solution | 2.00 |
| Water | 78.00 |
|  | 100.00 |

An alternative to preparing the ethylcellulose dispersion by the procedures described heretofore, for whatever reasons, may be more convenient for some manufacturers to make use of a pre-made ethylcellulose dispersions that are marketed by DOW CHEMICAL under the experimental names of XD-30543.40 and XD-3054.30. To illustrate the composition of such a pre-made dispersion the following example is being provided:

EXAMPLE 5

DOW Chemical's Ethylcellulose Dispersion XD-30543.40

| INGREDIENTS | PERCENT BY WEIGHT |
| --- | --- |
| Ethylcellulose | 18.70 |
| Plasticizers* | 6.20 |
| Ammonium Hydroxide | 1.30 |
| Water | 73.80 |
|  | 100.00 |

*A blend of dibutyl sebacate and a surface active agent.

Using the ethylcellulose dispersion described heretofore, water-proof sunscreen compositions may be made in a variety of ways to those skilled in the arts. In one procedure, using the ethylcellulose dispersion described in example 5, the ethylcellulose dispersion and an active sunscreen agent are combined in a suitable vessel. The sunscreen agent is added to the dispersion slowly with mixing until it is fully absorbed into the dispersion at room temperature. Upon completion, water is added to the mixture. If the pH of the composition drops below 9 it can be adjusted with ammonium hydroxide. The resulting composition is a liquid of low viscosity having an appearance and consistancy of milk and could very easily be marketed as a water-proof sunscreen "milk" lotion. To illustrate compositions prepared using the foregoing procedure, the following example is provided:

EXAMPLE 6

| INGREDIENTS | PERCENT BY WEIGHT |
| --- | --- |
| Ethylcellulose Dispersion (Ex. 5) | 10.00 |
| Padimate O | 8.00 |
| Water | 82.00 |
| | 100.00 |

To form water-proof sunscreen compositions having higher viscosities, a unique method is used by first preparing a dispersion of an acrylic acid crosslinked polymer with water and/or ethanol in a suitable vessel with high agitation until no agglomerates exists. This dispersion is then added, with agitation to a suitable vessel containing the ethylcellulose dispersion as described in Example 1. The acrylic acid crossed linked polymer combines with the alkaline dispersion promoting agent (ammonium hydroxide), which is contained in the ethylcellulose dispersion, forming compositions which can range in viscosity from viscous lotions to creams. The composition is then adjusted to a pH of about 9 with an ammonium hydroxide solution. Compositions prepared using such a procedure are represented in the following two examples:

EXAMPLE 7

| INGREDIENTS | PERCENT BY WEIGHT |
| --- | --- |
| Ethylcellulose Dispersion (Ex. 1) | |
| Ethylcellulose, STD vis 10 | 1.0 |
| Padimate O | 4.0 |
| Ammonium Hydroxide - 28% solution | 0.4 |
| Myristic Acid | 0.4 |
| Water | 4.2 |
| Acrylic Acid Dispersion | |
| Carbopol 940 | 0.5 |
| Water | 79.5 |
| Ammonium Hydroxide Solution | |
| Water | 9.9 |
| Ammonium Hydroxide - 28% solution | 0.1 |
| | 100.0 |

EXAMPLE 8

| INGREDIENTS | PERCENT BY WEIGHT |
| --- | --- |
| Ethylcellulose Dispersion (Ex. 1) | |
| Ethylcellulose, STD vis 10 | 1.00 |
| Padimate O | 4.00 |
| Ammonium Hydroxide - 28% solution | 0.40 |
| Myristic Acid | 0.40 |
| Water | 4.20 |
| Acrylic Acid Dispersion | |
| Carbopol 940 | 0.25 |
| Ethanol | 12.00 |

| INGREDIENTS | PERCENT BY WEIGHT |
| --- | --- |
| Padimate O | 4.00 |
| Ethylhexyl p-Methoxycinnamate | 4.00 |
| Ammonium Hydroxide Solution | |
| Water | 69.70 |
| Ammonium Hydroxide - 28% solution | 0.05 |
| | 100.00 |

Another procedure for making water-proof sunscreen compositions in the form of viscous lotions or creams is by the use of thickening agents whose thickening ability is not induced by chemical means. To those skilled in the arts, the use of such thickening agents and the manner in which they are incorporated into the compositions are well known. In one procedure using natural and synthetic gums, the gums are first dissolved in the portion of the water to be used in the compositions in a suitable vessel. Once the gum is dissolved, the optional ingredients, such as water-soluble organic liquids and the solid particulate matter can then be added. Upon completing the addition of any optional ingredients, a mixture of the active sunscreen agent and the ethylcellulose dispersion, as prepared in Example 3, is added to the gum solution. The composition is prepared at ambient conditions, however it has been observed, that heating the water before the addition of the gum is made, decreases the manufacturing time in preparing the composition. An ammonium hydroxide solution is added to the composition with agitation until a pH of about 9 is obtained. To illustrate compositions prepared using the foregoing procedure the following two examples are provided:

EXAMPLE 9

| INGREDIENTS | PERCENT BY WEIGHT |
| --- | --- |
| Ethylcellulose Dispersion (Ex. 3) | |
| Ethylcellulose, STD vis 10 | 1.00 |
| Padimate O | 8.00 |
| Myristic Acid | 1.00 |
| Ammonium Hydroxide - 28% solution | 1.00 |
| Water | 39.00 |
| Gum Solution | |
| Hydroxyethyl Cellulose | 1.00 |
| Water | 48.95 |
| Ammonium Hydroxide - 28% solution | 0.05 |
| | 100.00 |

EXAMPLE 10

| INGREDIENTS | PERCENT BY WEIGHT |
| --- | --- |
| Ethylcellulose Dispersion (Ex. 2) | |
| Ethylcellulose, STD vis 10 | 1.00 |
| Padimate O | 2.00 |
| 2-Ethylhexyl Salicylate | 2.00 |
| Myristic Acid | 0.40 |
| Ammonium Hydroxide - 28% solution | 0.40 |
| Water | 4.20 |
| Gum Solution | |
| Xanthan Gum | 0.75 |
| Ethanol | 21.00 |
| Oxybenzone | 4.00 |
| Water | 64.00 |
| Ammonium Hydroxide - 28% solution | 0.05 |
| | 100.00 |

Still another procedure for making water-proof sunscreen compositions in the form of viscous lotions or creams using thickening agents which do not react by chemical means, and in which the thickening agent is not dissolved in the composition, are thickening agents that are dispersed by physical means such as heat or high shear. In one procedure an inorganic compound, such as colloidal magnesium aluminum silicate, sold by (R. T. VANDERBUILT CO., NORWALK, CONN.) under the tradename of VEE GUM, is combined with the portion of the water to be used in the composition with agitation in a suitable vessel and heated to 90 degrees C. until the thickening agent is fully swollen. The dispersion is cooled to room temperature at which time a mixture of the active sunscreen agent and ethylcellulose dispersion as prepared in Example 4 is added and mixed until homogeneous. To the composition ammonium hydroxide is added with agitation, until a pH of about 9 is obtained. To illustrate compositions prepared using the foregoing procedure the following example is provided:

EXAMPLE 11

| INGREDIENTS | PERCENT BY WEIGHT |
| --- | --- |
| Ethylcellulose Dispersion (Ex. 4) | |
| Ethylcellulose, STD vis 10 | 1.00 |
| Padimate O | 4.00 |
| Ethylhexyl p-Methoxycinnamate | 4.00 |
| Myristic Acid | 1.00 |
| Ammonium Hydroxide | 1.00 |
| Water | 39.00 |
| Vee Gum Dispersion | |
| Vee Gum - HV | 4.00 |
| Water | 45.95 |
| Ammonium Hydroxide - 28% solution | 0.05 |
| | 100.00 |

A still further procedure for preparing water-proof sunscreen composition in the form of viscous lotions or creams is by the use of the in-situ formation of soaps. In this procedure, a fatty acid, such as stearic acid is combined with the active sunscreen agent in a suitable vessel; if desired a water-insoluble emollient such as cetyl alcohol ca be added to the composition at this time. This mixture, to those skilled in the arts is called the oil phase of the composition, is heated to about 85 degrees C. until a complete solution is formed. To a separate vessel water and triethanolamine are mixed together with any desired water soluble organic compound. This mixture is referred to as the water phase of the composition and is also heated to 85 degrees C. When both phases are at 85 degrees C., the water phase is added to the oil phase with agitation. The composition is cooled to a temperature betwen 40-65 degrees C. at which time the ethylcellulose dispersion, as illustrated in Example 5, is added with agitation. At this time if it is desired, particulate matter may be added to the composition which is then further cooled to room temperature. To illustrate compositions prepared using the foregoing procedure, the following examples are provided:

EXAMPLE 12

| INGREDIENTS | PERCENT BY WEIGHT |
| --- | --- |
| Oil Phase | |
| Stearic Acid | 4.00 |
| Cetyl Alcohol | 1.00 |
| Diisopropyl Adipate | 5.00 |
| Padimate O | 8.00 |
| Water Phase | |
| Water | 66.00 |
| Triethanolamine | 1.00 |
| Ethylcellulose Dispersion (Ex. 5) | 15.00 |
| | 100.00 |

EXAMPLE 13

| INGREDIENTS | PERCENT BY WEIGHT |
| --- | --- |
| Oil Phase | |
| Stearic Acid | 5.00 |
| Cetyl Alcohol | 1.00 |
| Mineral Oil | 3.00 |
| Padimate O | 8.00 |
| Oxybenzone | 3.00 |
| Water Phase | |
| Water | 49.00 |
| Triethanolamine | 1.00 |
| Ethylcellulose Dispersion (Ex. 5) | 20.00 |
| Particulate Matter | |
| Titanium Dioxide | 10.00 |
| | 100.00 |

An additional procedure for preparing water-proof sunscreen compositions in the form of viscous lotions or creams is by the use of surface active agents. In this procedure the surface active agent, the active sunscreen agents and any compatible optional ingredient are combined in a vessel and heated to 75 degrees C. and is called the oil phase. To a separate vessel water and any water-soluble optional ingredients are combined and heated to 75 degrees C. When both phases are at 75 degrees C., the water phase is added to the oil phase with agitation. The composition is cooled to 40 to 60 degrees C. at which point the ethylcellulose dispersion, as illustrated in Example 5, is added with agitation. At this point it is also convenient to add to the composition any particulate matter. The composition is then further cooled to room temperature with agitation. To illustrate compositions prepared using the foregoing procedure the following example is provided:

EXAMPLE 14

| INGREDIENTS | PERCENT BY WEIGHT |
| --- | --- |
| Oil Phase | |
| Cerasynt WN* | 5.00 |
| Padimate O | 8.00 |
| Water Phase | |
| Water | 66.50 |
| Propylene Glycol | 0.50 |
| Ethylcellulose Dispersion (Ex. 5) | 20.00 |
| | 100.00 |

*Cerasynt WN is a mixture of Glyceryl Stearate, Stearyl Alcohol and Sodium Lauryl Sulfate and is sold by the VanDyk Co., Belleville, NJ.

The examples illustrated hereintofore were applied on the skin and allowed to dry for fifteen minutes. They were then tested using the prescribed water resistancy test method described in the Federal Register Volume 43, number 166, and were considered to be resistant to removal from the skin by water and perspiration while maintaining their dry SPF value for periods of up to 80 minutes.

What I claim is:

1. A water-proof sunscreen composition comprising:
   A. from about 15% to about 95% by weight of water;
   B. from about 0.1% to about 6.0% by weight of ethylcellulose polymer having an average ethoxyl substitution of about 2.25 to about 2.58 on each anhydroglucose unit which equates to an ethoxyl content from about 45% to about 52%;
   C. from about 1.0% to about 30.0% by weight of an active ultraviolet radiation absorber;
   D. from about 0.01% to about 12% by weight of a surface active agent; and
   E. from about 0.03% to about 5.0% by weight of an alkaline dispersion promoting agent.

2. A water-proof sunscreen composition according to claim 1 wherein said ultraviolet radiation absorbers are selected from a group consisting of para-aminobenzoic acid; 2-ethoxyethyl p-methoxycinnamate; diethanolamine p-methoxycinnamate; digalloyl trioleate; 2,2′dihydroxy-4-methoxybenzophenone; ethyl 4-[bis(-hydroxypropyl)]aminobenzoate; 2-ethylhexyl salicylate; glyceryl aminobenzoate; 2-ethylhexyl 2-cyano-3,3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxbenzene sulfonic acid; triethanolamine salicylate; 4-tert. butyl-4 -methoxy-dibenzoylmethane; and benzalphthalide.

3. A water-proof sunscreen composition according to claim 1 where said alkaline dispersion promoting agents are selected from a group consisting of $C_3$–$C_6$ alkylamines, $C_3$–$C_6$ alkanolamines and ammonium hydroxide.

4. A water-proof sunscreen composition according to claim 1 where said surface active agents are selected from a group consisting of nonionic esters, nonionic ethers, sodium alkyl benzene sulfonates, sodium alkyl sulfates, sodium ethoxylated alkyl sulfates and soaps of a fatty acid and alkali.

5. A water-proof sunscreen composition specified in claim 1 which additionally comprises:
   A. from about 0% to about 20% by weight of a water-insoluble organic emollient compound having a water-solubility of less than 1% at 25 degrees C. selected from a group consisting of fatty alcohols, fatty acids, esters of fatty acids, esters of dicarboxylic acids, ethers of polypropylene glycol, alkanes and polysiloxanes;
   B. from about 0% to about 8% by weight of a plasticizer having a melting point less than 10 degrees C. selected from the group consisting of esters of benzoic acid, phthalic acid, adipic acid, succinic acid, sebacic acid and acetic acid;
   C. from about 0% to about 25% by weight of a water-soluble organic liquid compound having a water-solubility greater than about 2.5% at 25 degrees C. selected from a group consisting of monohydric alcohols, dihydric alcohols, trihydric alcohols, polyhydric alcohols, esters and ethers;
   D. from about 0% to about 20% by weight of suspended particulate solid matter;
   E. from about 0% to about 5% by weight of a thickening agent selected from a group consisting of natural gums, synthetic polymers, and inorganic salts; and
   F. from about 0% to about 3% by weight of a fragrance oil.

6. A water-proof sunscreen composition as specified in claim 5 wherein:
   A. said active ultraviolet radiation absorber is selected from a group consisting of paraaminobenzoic acid; 2-ethoxyethyl p-methoxycinnamate; diethanolamine p-methoxycinnamate; digalloyl trioleate; 2,1′-dihydroxy-4-methoxybenzophenone; ethyl 4-[bis (hydroxypropyl)]aminobenzoate; 2-ethylhexyl salicylate; glyceryl aminobenzoate; 2-ethylhexyl 2-cyano-3,3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert. butyl-4-methoxydibenzoylmethane; and benzalphthalide;
   B. said alkaline dispersion promoting agent is selected from a group consisting of diisopropanolamine and ammonium hydroxide;
   C. said plasticizer is selected from a group consisting of dibutyl sebacate and dibutyl phthalate;
   D. said surface active agent is selected from a group consisting of ammonium myristate, potassium oleate, triethanolamine stearate, sodium lauryl sulfate, polyoxyethylene sorbitan monolaurate and polyoxyethylene nonyl phenyl ether;
   E. said water-insoluble emollient is selected from a group consisting of cetyl alcohol, oleic acid, diisopropyl adipate, polyoxypropylene (14) butyl ether, mineral oil, and dimethylpolysiloxane;
   F. said water-soluble organic liquid is selected from a group consisting of ethanol, isopropanol, propylene glycol, glycerol, glycerol triacetate and diethylene glycol monoethyl ether;
   G. said suspended particulate solid matter is selected from a group consisting of aluminumized acrylic polyester, and metallic oxide; and
   H. said thickening agent is selected from a group consisting of xanthan gum, hydroxyethylcellulose, an acrylic acid crosslinked polymer, fumed silica, amorphous silica, sodium magnesium silicate and colloidal magnesium aluminum silicate.

7. A water-proof sunscreen composition consisting of active ultraviolet radiation absorbers comprising:
   A. from about 0.5% to about 2.0% by weight of ethylcellulose polymer having an average ethoxyl substitution of about 2.25 to about 2.58 on each anhydroglucose unit which equates to an ethoxyl content from about 45.0% to about 52.0% and a viscosity polymer molecule designation from about 4 to about 50;
   B. from about 25% to about 85% by weight of water;
   C. from about 2% to about 16% by weight of an active ultraviolet radiation absorber selected from a group consisting of para-aminobenzoic acid; 2-ethoxyethyl p-methoxycinnamate; diethanolamine-p-methoxycinnamate; digalloyl trioleate; 2,2′-dihydroxy-4-methoxybenzophenone; ethyl 4-[bis(hydroxypropyl)]-aminobenzoate; 2-ethylhexyl salicylate; glyceryl aminobenzoate; 2-ethylhexyl 2-cyano-3,3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert. butyl-4-methoxy-dibenzoylmethane; and benzalphthalide.

D. from about 0.2% to about 5.0% by weight of a plasticizer selected from a group consisting of dibutyl sebacate and dibutyl phthalate;

E. from about 0.1% to about 1.0% by weight of an alkaline dispersion promoting agent selected from a group consisting of diisopropanol-amine and ammonium hydroxide;

F. from about 0.5% to about 8% by weight of a surface active agent selected from a group consisting of ammonium myristate, potassium oleate, triethanolamine stearate, sodium lauryl sulfate, polyoxyethylene sorbitan monolaurate and polyoxyethylene nonyl phenyl ether;

G. from about 0.5% to about 2% by weight of a thickening agent selected from a group consisting of xanthan gum, hydroxyethylcellulose, an acrylic acid cross-linked polymer, modified copolymer of methyl vinyl ether and maleic anhydride, fumed silica, amorphous silica, sodium magnesium silicate and colloidal magnesium aluminum silicate;

H. from about 4.0% to about 10% by weight of a water-insoluble emollient selected from a group consisting of cetyl alcohol, oleic acid, diisopropyl adipate, polyoxypropylene (14) butyl ether, mineral oil, and dimethylpolysiloxane;

I. from about 5.0% to about 15% by weight of a water-soluble liquid organic compound selected from a group consisting of ethanol, isopropanol, propylene glycol, glycerol, glycerol triacetate and diethylene glycol monoethyl ether; and J. from about 5.0% to about 15% by weight of suspended particulate solid matter selected from a group consisting of aluminumized acrylic polyester, and metallic oxides.

8. A water-proof sunscreen composition according to claim 7 wherein the active ultraviolet radiation absorber is Padimate O.

9. A water-proof sunscreen composition according to claim 7 wherein the active ultraviolet radiation is Oxybenzone.

10. A water-proof sunscreem composition according to claim 7 wherein the active ultraviolet radiation absorber is ethyl 4-bis[(hydroxypropyl)]aminobenzoate.

11. A water-proof sunscreen composition according to claim 8 wherein the active ultraviolet radiation absorber is ethyl p-methoxycinnamate.

12. A water-proof sunscreen composition according to claim 7 wherein the active ultraviolet radiation absorber is Padimate O and Dioxybenzone.

13. A water-proof sunscreen composition according to claim 7 wherein the ethylcellulose polymer is an ethylcellulose having an ethoxyl substitution between 48.0% to 49.5%.

14. A water-proof sunscreen composition according to claim 7 wherein the plasticizer is dibutyl sebacate.

15. A water-proof sunscreen composition according to claim 7 wherein the alkaline dispersion promoting agent is ammonium hydroxide.

16. A water-proof sunscreen composition according to claim 7 wherein the surface active agent is ammonium myristate.

17. A water-proof sunscreen composition according to claim 7 wherein the surface active agent is triethanolamine stearate.

18. A water-proof sunscreen composition according to claim 7 wherein the suspended particulate matter is colorized acrylic polyester.

19. A water-proof sunscreen composition according to claim 7 wherein the suspended particulate matter is zinc oxide.

20. A water-proof sunscreen composition according to claim 7 wherein the suspended particulate matter is titanium dioxide.

21. A water-proof sunscreen composition according to claim 7 wherein the water insoluble liquid emollient is polyoxypropylene (14) butyl ether.

22. A water-proof sunscreen composition according to claim 7 wherein the water insoluble liquid emollient is diisopropyl adipate.

23. A water-proof sunscreen composition according to claim 7 wherein the thickening agent is an acrylic acid crosslinked polymer having a molecular weight from about 3,500,000 to about 4,500,000.

24. A water-proof sunscreen composition according to claim 7 wherein the thickening agent is colloidal magnesium aluminum silicate.

25. A water-proof sunscreen composition according to claim 7 wherein the water-soluble organic liquid compound is ethanol.

26. A process for preparing a water-proof sunscreen composition which comprises from 15% to about 95% water, from about 0.1% to about 6% by weight of ethylcellulose polymer having an average ethoxyl substitution of about 2.25 to about 2.58 on each anhydroglucose unit which equates to an ethoxyl content from about 45% to about 52%, from about 1% to about 30% by weight of an active sunscreen agent, from about 0.1% to about 12% by weight of a surface active agent and from about 0.03% to about 5.0% by weight of an alkaline dispersion promoting agent comprising the step of forming a collodial dispersion of ethylcellulose/active sunscreen agent by varying the temperature and the time so that particles are formed having an average diameter of less than 1 micron, that when applied to the skin coalesce, to form a continuous, impervious water-resistant film.

27. A process of claim 26 wherein the ethylcellulose has a degree of substitution of ethoxyl group of about 2.25 to 2.58 and a viscosity designation between 4 and 50.

28. A process of claim 26 wherein the active sunscreen agent is selected from a group consisting of 2-ethoxyethyl p-methoxycinnamate; diethanolamine p-methoxycinnamate; digalloyl trioleate; ethyl 4-[bis(hydroxypropyl)]aminobenzoate; 2-ethylhexyl salicylate; glyceryl aminobenzoate; 2-ethylhexyl 2-cyano-3,3-diphenylacrylate; ethylhexyl p-methoxycinnamate; 3,3,5-trimethylcyclohexyl salicylate; menthyl o-aminobenzoate; triethanolamine salicylate; amyl p-dimethylaminobenzoate; and octyl p-dimethylaminobenzoate.

29. The process of claim 26 wherein the surface active agent is a soap of a fatty acid and an alkali or a metal.

30. The process of claim 26 wherein the alkaline dispersion promoting agent is ammonium hydroxide.

31. The process of claim 26 wherein the alkaline dispersion promoting agent is triethanolamine.

32. The process of claim 26 wherein the steps of forming the ethylcellulose/active sunscreen agent dispersion, serves simultaneously to form the surface active agent by the formation of a soap of a $C_{12}$–$C_{18}$ fatty acid and an alkali or a metal.

33. The process of claim 26 comprising the steps of:
A. dispensing the fatty acid in the active sunscreen agent,
B. heating the mixture with agitation to a temperature and for a time sufficient to produce a clear solution,
C. adding the ethylcellulose,
D. heating the mixture with agitation to a temperature between 100 degrees C. to about 120 degrees C. until the ethylcellulose dissolves,
E. cooling the mixture with agitation to a temperature from about 75 degrees C. to about 100 degrees C.,
F. adding a solution of ammonium hydroxide and water which has previously been heated to a temperature from 75 degrees C. to 100 degrees C., and
G. cooling the mixture with agitation to room temperature.

34. The process of claim 33 wherein the active sunscreen agent is octyl p-dimethylaminobenzoate.

35. The process of claim 33 wherein the fatty acid is myristic acid.

* * * * *